(12) United States Patent
Witham (10) Patent No.: US 8,671,874 B2
(45) Date of Patent: Mar. 18, 2014

(54) PROCESS AND APPARATUS FOR LOCALIZED COATING OF ASSEMBLED CASCADE IMPACTOR PARTICLE COLLECTION SURFACES

(76) Inventor: Clyde L. Witham, Saratoga Springs, UT (US)

( * ) Notice: Subject to any disclaimer, the term of this patent is extended or adjusted under 35 U.S.C. 154(b) by 61 days.

(21) Appl. No.: 13/257,306

(22) PCT Filed: Mar. 17, 2010

(86) PCT No.: PCT/US2010/027574
§ 371 (c)(1),
(2), (4) Date: Sep. 18, 2011

(87) PCT Pub. No.: WO2010/107858
PCT Pub. Date: Sep. 23, 2010

(65) Prior Publication Data
US 2012/0009330 A1    Jan. 12, 2012

Related U.S. Application Data

(60) Provisional application No. 61/162,139, filed on Mar. 20, 2009.

(51) Int. Cl.
| | | |
|---|---|---|
| *B05B 1/12* | (2006.01) | |
| *B05B 15/04* | (2006.01) | |
| *B05B 7/02* | (2006.01) | |
| *B05D 1/02* | (2006.01) | |
| *B05D 5/00* | (2006.01) | |
| *B05D 7/22* | (2006.01) | |

(52) U.S. Cl.
USPC .................... 118/317; 427/230; 427/421.1

(58) Field of Classification Search
USPC ............. 427/230–239, 421.1–427.7; 118/317
See application file for complete search history.

(56) References Cited

U.S. PATENT DOCUMENTS

| | | |
|---|---|---|
| 4,290,384 A | 9/1981 | Ausschnitt et al. |
| 4,586,389 A | 5/1986 | Vincent et al. |
| 4,640,140 A | 2/1987 | Burghoffer et al. |
| 6,435,043 B1 | 8/2002 | Ferguson et al. |
| 6,723,568 B1 | 4/2004 | Liu et al. |
| 2008/0047372 A1 | 2/2008 | Bridge et al. |
| 2010/0288057 A1* | 11/2010 | Witham ..................... 73/863.22 |

OTHER PUBLICATIONS

Huang, Cheng-Hsiung, et al., "Particle collection efficiency of an inertial impactor with porous metal substrates" Aerosol Science 32:1035-1-44, 2001.
Nasr, Moheb M, et al, "Effect of drug load and plate coating on the particle size distribution of a commercial albuterol metered dose inhaler (MDI) using Andersen and Marple-Miller cascade impactors" Pharmaceutical Research 14 (10):1437-1443, 1997.
Cox, Christopher S and Wathes, Christopher M editors, Bioaerosols Handbook, CRC Prress 1995, pp. 204-206.

* cited by examiner

*Primary Examiner* — William Phillip Fletcher, III (57) ABSTRACT

Methods are presented for applying a coating material to the particle collecting regions and surfaces of the stages of a cascade impactor after the impactor is assembled for use. The methods comprise generation of a multimodal droplet aerosol of liquid coating material and delivering it into the impactor. The modes of coating droplet aerosol are selected to produce droplets that span the range of cutoff diameters for the stages of the cascade impactor. The coating substance improves the trapping of particles on the stages. The methods limit the total amount of coating material applied and confine it to the regions of particle impact opposite the stage orifices, thereby reducing the possibility of chemical interference when analyzing a test aerosol.

31 Claims, 3 Drawing Sheets

Figure 8

PROCESS AND APPARATUS FOR LOCALIZED COATING OF ASSEMBLED CASCADE IMPACTOR PARTICLE COLLECTION SURFACES

CROSS-REFERENCE TO RELATED APPLICATIONS

This application claims the benefit of U.S. Provisional Application No. 61/162,139 filed 20 Mar. 2009, and PCT/US2010/027574 filed 17 Mar. 2010, which are incorporated herein by reference.

FIELD OF THE INVENTION

The invention relates to apparatus and methods for coating the particle collection surfaces of cascade impactors.

BACKGROUND OF THE INVENTION

Cascade impactors are devices used to segregate and quantify aerosol particle size distributions based upon aerodynamic and other properties. Some cascade impactors collect the aerosol particles on filter media. The majority and most common cascade impactors utilize metal plates as the collection surface. In some devices this metal collection surface is the top of the next collection stage. In others, it is a separately inserted collection plate. Nevertheless, in order to avoid bounce-off and blow-off of the particles from the collection surface, it is common to apply a coating such as grease or other sticky substance to trap and retain the particles.

Trapping and retention of the aerosol particles on the proper stage is paramount to determining the correct size distribution. But also important is the need to assure that the coating substance, while present at an amount effective to trap and retain the particles, does not interfere with the subsequent analysis. Interference can occur through physical and/or chemical means. Interference with chemical analyses will be related to the quantity or mass of the coating material on each stage in relationship to the mass of aerosol particles to be assayed.

Conventional methods for coating impactor collection plates have involved spraying them in ventilated fume hoods or on the counter top with grease from pressurized containers. Other methods involve dipping the plates into, or using a pipette to flood the tops of them with, a solution or suspension of the coating material and allowing the coating to dry to a sticky consistency before loading the plates into the impactor. These methods provide poor control over the total amount of coating material applied and thus no reliable means to avoid interference with the chemical assays.

Thus there is a need to assure efficient particle trapping with minimal assay interference by applying the coating materials only where they are needed; that is, only where the aerosol particles will be impacting the collection plates or surfaces. This area is referred to as the particle-collecting regions of the collection substrates, collection surfaces, or stages. These areas are distinct from the other regions of the substrates and other structural portions of the impactor such as the walls and orifice plates.

SUMMARY OF THE INVENTION

The foregoing and further needs are satisfied by embodiments of the invention.

Novel apparatuses and methods have been developed to apply a suitable coating to the collection surfaces of the stages of cascade impactors in the region directly opposing the orifices of the stages. The coating is deposited exactly where the aerosol to be analyzed will be impacted and deposited. The methods and apparatuses provide for limiting application of extraneous coating to any other part of the impactor or collection substrates. The apparatuses and methods serve to form and deliver an aerosol of the coating material. The aerosol may be drawn through the impactor under normal operating conditions or conveyed through the impactor by the flow produced by the apparatus.

It has been discovered that a very wide and multimodal aerosol size distribution of coating-material droplets is required so that each impactor stage is effectively coated. It has been found that such an aerosol can be generated by modification and control of several atomization techniques known in the art, including rotary (e.g., spinning disc), hydraulic (e.g., liquid spray under pressure), pneumatic (e.g., twin fluid atomization), electrohydrodynamic, vibrating orifice, vibrating mesh, or other atomization techniques as are known in the art. An aerosol may also be produced by dissolution or suspension of the coating material in a suitable propellant (e.g., chlorofluorocarbon, hydrogen chlorofluorocarbon, hydrocarbon, nitrogen, carbon dioxide, etc.) and generating a spray from the resulting propellant pressure.

In some embodiments, the invention comprises an apparatus for localized coating of the collection surfaces of a cascade impactor comprising a plurality of aerosol generators operating to produce coating aerosol droplets with different mass median aerodynamic diameters.

In some embodiments, the coating aerosol droplets are delivered to the impactor collection surfaces under positive pressure produced by the apparatus.

In some embodiments, the aerosol size distribution of the coating droplets is controlled by individually varying the air pressure applied to a plurality of jet nebulizers.

In other embodiments, the coating aerosol droplets are delivered to the impactor collection surfaces by drawing a vacuum at the outlet of the cascade impactor.

In still other embodiments, a vacuum source is applied to the outlet of the impactor and the coating aerosol is supplied at atmospheric or at a pressure above atmospheric at the inlet to the impactor.

In some embodiments, the invention comprises an apparatus for localized coating of the collection surfaces of a cascade impactor comprising an aerosol generator operating to produce coating aerosol droplets having size distributions with different mass median aerodynamic diameters, wherein the output of the aerosol generator is directable to the inlet of the cascade impactor.

In some embodiments, the aerosol size distribution of the coating droplets is controlled by varying the feed rate of liquid coating material to one or more aerosol generators.

In some embodiments, the invention comprises a method for localized coating of the collection surfaces of a cascade impactor comprising generating a multimodal coating droplet aerosol with a plurality of aerosol generators and directing the aerosol through the impactor.

In some embodiments, the method comprises aerosol generators that are jet nebulizers.

In other embodiments, the invention comprises a method for localized coating of the collection surfaces of a cascade impactor comprising operating an aerosol generator to produce coating aerosol droplets having size distributions with different mass median aerodynamic diameters and directing said droplets to the inlet of the impactor.

In some embodiments, the method comprises varying the supply rate of coating solution or suspension to the aerosol generator.

In some embodiments, the method comprises forcing the coating aerosol droplets through the impactor under positive pressure.

In some embodiments, the method comprises drawing the coating aerosol droplets through the impactor under a vacuum.

In still other embodiments, the method comprises simultaneously forcing the coating aerosol droplets through the impactor under positive pressure and simultaneously drawing the coating aerosol droplets through the impactor under a vacuum.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 shows dual nebulizer heads corresponding to several embodiments of the invention.

DETAILED DESCRIPTION OF THE INVENTION

The invention provides embodiments for apparatuses and methods for depositing a localized coating on and in the particle collecting regions of the particle collection surfaces of cascade impactors.

As used herein, the terms "comprising", "including", "such as", and "for example" are used in their open, non-limiting sense.

As used herein, the term "about" is used synonymously with "approximately." As such, values ranging between ±20% of the stated value may be considered equivalent for pressures and flow rates and ±30% for particle sizes.

As used herein, the term "aerosol" is defined as a suspension of solid particles or liquid droplets in air.

As used herein, the terms "atomizer", "atomizer head", "nebulizer", and "aerosol generator" and their plural forms are used interchangeably to describe apparatuses or devices that produce droplets from liquid or from a suspension of particles or micelles in a liquid.

As used herein, the terms "impactor plate", "particle collection substrate", and "particle collection surface" and their plural forms are used interchangeably to indicate the region, portion or component of the cascade impactor which is analyzed for collected aerosol material. In some impactors, this is a removable plate or substrate. In other impactors it is a non-removable region that is rinsed for recovery of the aerosol particles.

As used herein, the terms "cutpoint", "cut size", and "cutoff diameter" refer to the median particle collection diameter for a given stage in a cascade impactor.

To produce a suitable localized coating in the particle-collecting regions of each substrate or collection surface in a cascade impactor, it is necessary to produce an aerosol of coating droplets with an overall size distribution that is broad enough to deposit a sufficient mass of coating in the particle impaction regions of each of the collection substrates or surfaces. A typical aerosol generator such as a nebulizer will produce a size distribution that is lognormal. That is, the logarithms of the particle diameters are normally distributed with respect to their frequency of occurrence. Depending upon the median size (typically the mass median aerodynamic diameter, MMAD) and the geometric standard deviation (GSD) of the distribution, there may be too little mass of smaller particles to deposit a sufficient coating on the collection surfaces associated with stages with small cutoff diameters and there may be too few large particles to adequately coat the collection surfaces associated with the stages having large cutoff diameters. This is because the typical aerosol generator produces a monomodal distribution and, although the total mass of coating material aerosol may be sufficiently high at the inlet of the impactor, the fractional mass remaining will be decreased as each stage removes particles of a size determined by the stage cutoff diameter. To overcome this limitation, broad aerosol size distributions and multimodal aerosol size distributions enriched with coating aerosol particles spanning the cutoff diameters of the stages are produced by embodiments of the invention.

The droplet size distribution from an aerosol generator can be controlled, for example, by varying a property of the fluid to be aerosolized (e.g. surface tension, viscosity, or density), the liquid feed rate, or the energy input to the atomizer with time. The energy input may be expressed, for example, as the rotation speed of a rotary atomizer, as the pressure applied to a pneumatic or hydraulic atomizer, as the vibrational frequency and amplitude of a vibrating orifice or vibrating mesh atomizer, or as the electrical potential applied to an electrohydrodynamic (EHD) or electrostatic atomizer.

The droplet size distributions from atomizers can also be controlled, for example, by varying fluid flow characteristics, e.g., the liquid to gas ratio of an effervescent atomizer or a pneumatic atomizer; by varying the dimensional parameters of the atomizer, e.g., orifice sizes, channel or feed-tube dimensions, aerosol chamber size; and by the presence or absence of an impaction surface or surfaces opposite the atomizer jet.

Suitable coating materials for particle collection in cascade impactors may be prepared in suspension or solution and can be selected from a variety of materials including but not limited to, for example, greases, oils and other petroleum based materials, silicone based lubricants, and waxes. Some investigators have also reported using glycerin, SPAN-85, and Vaseline. (Cox, C. C. and C. M. Wathes, *Bioaerosols Handbook*, CRC Press, 1995 pp. 204-205; Nasr, M N, et al., "Effect of Drug Load and Plate Coating on the Particle Size Distribution of a Commercial Albuterol Metered Dose Inhaler Determined Using the Andersen and Marple-Miller Cascade Impactors", *Pharmaceut Res* 14(10):1437-1443, 1997). Coating materials may be diluted, dissolved, or suspended in a variety of solvents including, for example, water, acetone, alcohol, alkanes, and other organic solvents, and dispersed by atomizers as described in the various embodiments presented herein.

In some embodiments, the invention comprises an apparatus for localized coating of the collection surfaces of a cascade impactor comprising a plurality of aerosol generators operating to produce coating aerosol droplets with different mass median aerodynamic diameters, wherein the aggregated output of said plurality of aerosol generators is directable to the inlet of the cascade impactor.

In some embodiments of the invention, the aerosol generators are selected from the group consisting of pneumatic atomizers, jet nebulizers, rotary atomizers, industrial atomizers, spinning disc aerosol generators, vibrating orifice generators, vibrating membrane generators, vibrating mesh generators, electrohydrodynamic nebulizers, electrostatic nebulizers, and combinations thereof.

In some embodiments of the invention, the apparatus comprises an aerosol generator comprising one or more dry powder aerosol generators.

In other embodiments of the invention, the apparatus comprises an aerosol generator comprising one or more jet nebulizers.

In other embodiments, the apparatus comprises two or more jet nebulizers, each comprising an orifice capable of controlling airflow and a channel and/or orifice capable of controlling liquid flow, assembled in a chamber.

In some embodiments of the invention the two or more jet nebulizers are each made with different size orifices and or channels. This results in different droplet size distributions and a multimodal aerosol having a broader size distribution than can be achieved with a single atomizer head.

In some embodiments, the two or more jet nebulizers are operated at a single pressure.

In other embodiments, each of the two or more jet nebulizers is operated at a different pressure.

In still other embodiments, the apparatus comprises three or more jet nebulizers, each comprising an orifice capable of controlling airflow and a channel and/or orifice capable of controlling liquid flow, assembled in a chamber.

In some embodiments, the apparatus comprises a number of aerosol generators equal to the number of stages in the cascade impactor whose collection substrates are to be coated.

In some embodiments the MMAD values of the coating aerosol droplets from the aerosol generators are approximately equal to the cutoff diameters for one or more of the individual stages of the impactor.

In some embodiments, the invention comprises an apparatus for localized coating of the collection surfaces of a cascade impactor comprising an aerosol generator operating to produce coating aerosol droplets having size distributions with different mass median aerodynamic diameters, wherein the output of said aerosol generator is directable to the inlet of the cascade impactor.

In some embodiments, a liquid pump controlled by a microprocessor varies the liquid rate to the aerosol generator. This produces a coating droplet size distribution that varies with time.

In some embodiments, the aerosol generators are contained within an atomizer chamber In some embodiments, the output of the atomizer chamber is connected to the input of the impactor.

In some embodiments, the outlet of the impactor is left open to the atmosphere.

In some embodiments, the coating suspension or solution is added to the atomizer chamber, atomized, and delivered through the impactor by virtue of the pressure and airflow created by the apparatus.

In some embodiments, additional auxiliary airflow is added to the output of the aerosol generators. The auxiliary airflow assists in carrying the coating aerosol droplets thru the impactor at an acceptable flow rate, typically, but not exclusively, the normal sampling flow rate of the impactor.

In some embodiments of the invention, the spray from the jet nebulizers is further broken up by directing the spray onto an impaction surface suspended just beyond the atomizer nozzles prior to delivery into the impactor.

In some embodiments, the reservoir for the nebulizers is filled with the exact amount of coating solution or suspension needed to coat a single impactor. In other embodiments the reservoir for the atomizers is filled with an amount of coating solution or suspension to allow multiple impactors to be coated.

In certain embodiments, the nebulizers are pressurized with air and the coating solution or suspension is aspirated into the atomizer heads. An impaction surface is placed opposite the atomized liquid jet to produce a more consistent aerosol size distribution. The aerosol is carried by the atomizing air into the impactor where it passes through the various orifices of the impactor stages and deposits on the collection surfaces just below the orifices. The air is exhausted through the outlet of the impactor.

In some embodiments, additional auxiliary airflow is added to assist in carrying the coating aerosol droplets thru the impactor at an acceptable flow rate, typically, but not exclusively, the normal sampling flow rate of the impactor.

In certain embodiments, coating is complete when the atomizer-chamber is emptied. In other embodiments, the atomizer air is switched off with a timer after the appropriate amount of coating material has been atomized.

In some embodiments, filtered dry compressed air is configured to flow through the impactor for a specified amount of time to dry the coating deposits on the impactor collection plates. A timer turns off the air. In some embodiments, the timer function is accomplished with a microprocessor.

In some embodiments, a solenoid valve diverts the airflow from the atomizer heads to the chamber where it flows through the impactor for a specified amount of time to dry the coating deposits on the impactor collection plates. A timer turns off the air. In some embodiments, the timer function is accomplished with a microprocessor.

In some embodiments of the invention, the coating liquid solution or suspension is pumped to the atomizer heads. In certain embodiments the liquid flow rate is varied with time. In other embodiments, the liquid flow is maintained at a constant rate depending on the range of droplet sizes desired.

In some embodiments of the apparatus, the air to the atomizer heads is pressurized and started. The liquid flow is then turned on for a specified time and controlled with either a microprocessor or timer. After a predetermined length of time, the liquid is turned off, and the filtered dry compressed air continues to flow. The air flows through the impactor for a specified amount of time and is shut off by a microprocessor or timer after the coating deposits on the collection surfaces of the impactor have dried.

In some embodiments of the invention, the impactor is connected to a vacuum source to draw air through it. In other embodiments of the invention, the outlet of the impactor is open to the atmosphere and airflow is induced by the positive flow and pressure created in the apparatus by either the atomizer flow, an auxiliary flow, or both. In some embodiments, a separate vacuum source is not necessary to draw the coating aerosol into the cascade impactor. In still other embodiments, a vacuum source is applied to the outlet of the impactor and the coating aerosol is supplied at atmospheric or at a pressure above atmospheric at the inlet to the impactor.

The atomizer heads and other components of the apparatus as described in the various embodiments of the invention may be constructed of metal, plastic, or glass, with the understanding that the material chosen must be compatible with the solvent used for dispersing the coating material solution or suspension. One of skill in the art would readily know how to choose a compatible material.

In some embodiments, the invention comprises a method for localized, in situ coating of the collection substrates of a cascade impactor comprising generating a multimodal aerosol of coating material droplets and delivering said aerosol to the cascade impactor.

In other embodiments, the method comprises generating a multimodal aerosol of droplets of coating material with one or more pneumatic atomizers, and delivering said aerosol to the cascade impactor. In still other embodiments, the method comprises generating a multimodal aerosol of droplets of coating material with two or more atomizing heads, each comprising an orifice capable of controlling airflow and a channel and/or orifice capable of controlling liquid flow, assembled in a chamber, and delivering said aerosol to the cascade impactor.

In still other embodiments, the method comprises generating a multimodal aerosol of droplets of coating material with three or more atomizing heads, each comprising an orifice capable of controlling airflow and a channel and/or orifice capable of controlling liquid flow, assembled in a chamber, and delivering said aerosol to the cascade impactor.

In still other embodiments, the method comprises generating a multimodal aerosol of droplets of coating material with a number of atomizing heads equal to the number of stages in the cascade impactor with collection substrates to be coated, each comprising an orifice capable of controlling airflow and a channel and/or orifice capable of controlling liquid flow, assembled in a chamber, and delivering said aerosol to the cascade impactor.

In certain embodiments, the method comprises generating coating aerosol droplets with MMAD values approximating the cutoff diameters for one or more of the individual stages of the impactor.

In some embodiments the invention comprises a method for coating of the collection substrates of a cascade impactor, comprising generating a multimodal aerosol of coating material droplets by varying the liquid flow rate to one or more aerosol generators and delivering said aerosol to the cascade impactor.

In some embodiments the liquid flow rate is varied by a microprocessor attached to a pump.

In some embodiments, the pump comprises a syringe pump. In other embodiments, the pump comprises a peristaltic pump. In still other embodiments, the pump comprises a rotary-vane or impeller-driven liquid pump.

In some embodiments the invention comprises a method for coating of the collection substrates of a cascade impactor, comprising generating a multimodal aerosol of coating material droplets, and delivering the aerosol to the impactor wherein the outlet of the impactor is left open to the atmosphere. The coating aerosol droplets are thereby delivered through the impactor by virtue of the pressure and airflow created by the apparatus generating the aerosol.

In some embodiments, the method comprises adding auxiliary airflow to deliver the aerosol through the impactor.

In some embodiments the invention comprises a method for coating of the collection substrates of a cascade impactor, comprising generating a multimodal aerosol of coating material droplets, and delivering the aerosol to the impactor wherein the outlet of the impactor is connected to a vacuum source to draw the aerosol there-through.

In some embodiments the method comprises adding auxiliary airflow to equal the total airflow sampled by the impactor.

Figure 1:
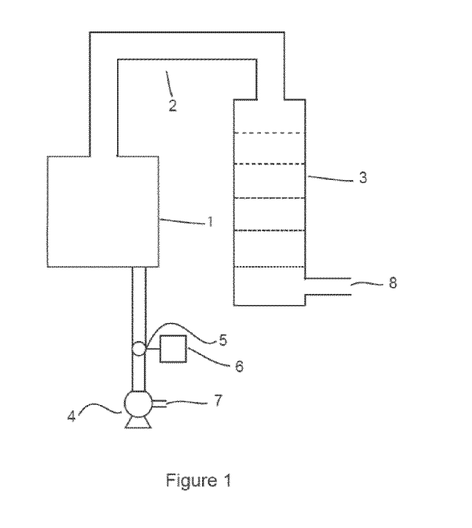
FIG. 1 is a diagram of a coating apparatus according to several embodiments of the invention.

Turning now to the figures, FIG. 1 is a block diagram of an embodiment wherein the solution or suspension of coating material is aspirated into the atomizer heads and the apparatus is operated until the liquid is gone. Air enters into the inlet 7 of the compressor 4 and is introduced into the atomizers through a valve 5. The valve is opened and closed with a solenoid that may be controlled either with a microprocessor or with a timer 6. The atomizers are inside the atomizer chamber 1 and produce drops of a wide size distribution. The aerosol thus produced is conveyed through a tube 2 to the impactor 3. The coating aerosol is deposited in the particle-collecting regions of the collection surfaces of the impactor, and the air is exhausted through the outlet of the impactor 7. When the liquid is fully atomized, the airflow remains flowing by means of the open valve thus drying the deposited coating. After a length of time sufficient to dry the coating material to a sticky surface, the timer closes the valve, and the air is shut off.

In some embodiments of the invention, the timer or microprocessor controls the drying time from between about 2 to about 20 minutes.

FIG. 1 and other figures and examples herein refer to a compressor as a source of airflow for the atomizer heads. One of skill in the art would readily recognize the ability to substitute a commercially available air pump or a tank of compressed air with sufficient capacity (volume and pressure) to operate the nebulizer heads and subsequently dry the coating material.

Figure 2:
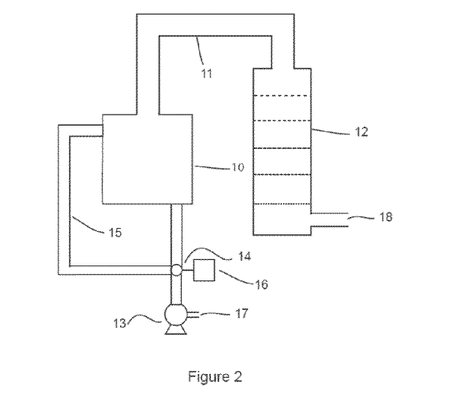
FIG. 2 is a diagram of a coating apparatus according to other embodiments of the invention.

FIG. 2 shows a block diagram of an embodiment of the apparatus wherein the liquid coating material solution or suspension is aspirated into the atomizer heads, and the apparatus is operated only long enough to adequately coat the impactor collection surfaces. Air enters into the inlet 17 of the compressor 13 and is introduced into the atomizers through a valve 14. The valve is opened and closed with a solenoid that is controlled either with a microprocessor or with a timer 16. The atomizers are inside the atomizer chamber 10 and produce aerosol droplets having a wide size distribution. The aerosol thus produced is conveyed through a conduit tube or pipe 11 to the impactor 12. The coating material aerosol is deposited on the collection surfaces of the impactor in the particle-collecting regions, and the air is exhausted through the outlet of the impactor 18. When an appropriate amount of adhesive aerosol has been deposited onto the impactor collection surfaces, the three way valve 14 which is controlled by the timer or microprocessor, is activated, and the compressed air is diverted away from the atomizer heads via a tube 15, and into the atomizer chamber 10, where it is conveyed to the impactor 18 and dries the deposited coating material. After a set time, the microprocessor or timer 16 actuates the valve 14 to shut off the drying air. Coating material liquid or suspension remaining in the atomizer chamber is then available for the next impactor to be coated.

Figure 3:
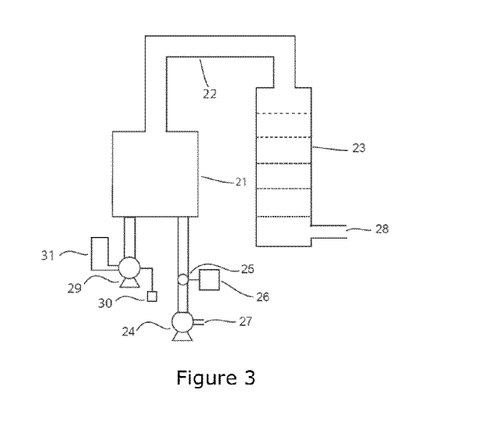
FIG. 3 is a diagram of a coating apparatus according to additional embodiments of the invention.

FIG. 3 shows yet another embodiment of the apparatus in which the coating material liquid or suspension is delivered at a controlled flow rate from a reservoir 31 by a liquid pump 29 that in turn is controlled by a microprocessor or timer 30. The coating material flow rate to the atomizers can be varied with time or held constant by the microprocessor according to methods known in the art. Air enters the inlet 27 of the compressor 24 and is introduced into the atomizer through a valve 25. The valve is opened and closed with a solenoid that is controlled either with a microprocessor or with a timer 26. The atomizers are inside the atomizer chamber 21 and produce drops of a wide size distribution. The aerosol thus produced is conveyed through a conduit tube or pipe 22 to the impactor 23. The adhesive aerosol is deposited in the particle-collecting regions of the collection surfaces of the impactor, and the air is exhausted through the outlet 28 of the impactor 23. When an appropriate amount of coating aerosol has been deposited onto the impactor collection surfaces, the timer or microprocessor 30 shuts off the liquid flow. The compressed air continues to flow and is conveyed to the impactor and dries the deposited coating. After a sufficient drying time for the coating, the timer or microprocessor 30 stops the airflow.

Figure 4:
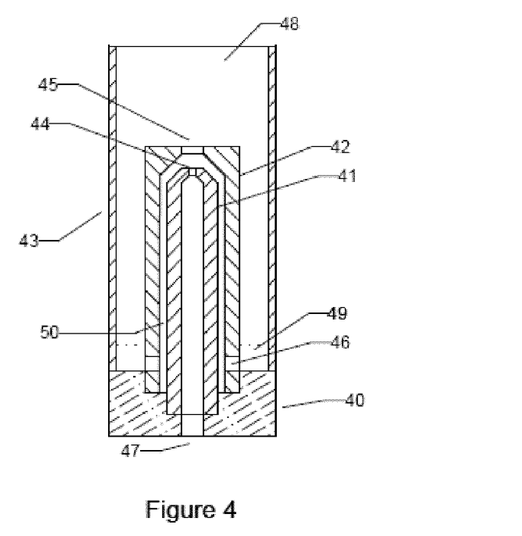
FIG. 4 shows a nebulizer head corresponding to several embodiments of the invention.

FIG. 4 is a depiction of a single atomizer head in an atomizer chamber according to various embodiments of the invention. In some embodiments of the apparatus, multiple atomizer heads are combined to achieve a mutimodal, broad size distribution of the coating material aerosol droplets. Compressed air is introduced into the atomizer head through the inlet 47 on the atomizer base 40. The air is exhausted under pressure through a first orifice 44 and then through a second orifice 45. The coating material liquid or suspension 49 is aspirated through the liquid inlet holes 46 in the outer sleeve 42 of the atomizer head. The action of the air expanding through the first orifice 44 of the inner sleeve 41 aspirates liquid into the liquid channel 50 and subsequently into the space between the first and second orifices 44 and 45. Air and liquid are mixed in the space and atomized upon exit from the atomizer head through the second orifice. An impaction surface (depicted in FIG. 6) may be placed just beyond the exit of the second orifice 45 to further break up the liquid droplets. The coating material aerosol is conveyed from the chamber 43 through the outlet 48.

The size distribution of the coating aerosol droplets will be dependent on the diameter of the first orifice 44, the diameter of the second orifice 45, and/or ratio of the diameters of the second and first orifices 44 and 45, the annular area of the liquid channel 50, the pressure of the air, and fluid properties of the coating material solution or suspension.

In some embodiments of the invention the first orifice 44 has a diameter of about 0.01 inches to about 0.1 inches. In other embodiments of the invention, the diameter of first orifice 44 is between about 0.0135 inches and about 0.08 inches, or between about 0.02 inches and about 0.05 inches.

In some embodiments of the invention the second orifice 45 has a diameter of about 0.012 inches to about 0.5 inches. In other embodiments of the invention, the diameter of second orifice 45 is between about 0.02 inches and about 0.2 inches, or between about 0.025 inches to about 0.1 inches, or between about 0.03 inches to about 0.05 inches.

In some embodiments of the invention the diameter of the second orifice 45 is defined in terms of the ratio of the second orifice 45 diameter to the first orifice 44 diameter. In some embodiments of the invention the ratio of the second orifice diameter to the first orifice diameter is between about 1 and about 5. In other embodiments, the ratio of the second orifice diameter to the first orifice diameter is between about 1.5 to about 5.0, between about 1.5 to about 3.0, or between about 1.8 to about 2.4. In still other embodiments, ratio of the second orifice diameter to the first orifice diameter is about 1, about 1.5, about 2, about 2.5, about 3, about 3.5, about 4, about 4.5, or about 5.

The number and diameter of liquid inlet holes 46 may be easily determined by one skilled in the art to achieve sufficient atomization of the coating aerosol material. In general there will need to be enough holes to ensure that liquid flow is not restricted into the channel 50. In general, the area of the liquid inlet holes needs to be larger than the annular area between the inner sleeve 41 and the outer sleeve 42.

In some embodiments of the invention the liquid inlet holes 46 have diameters between about 0.05 inches and about 0.25 inches. In other embodiments, the diameter of the liquid inlet holes 46 is between about 0.0625 inches and 0.125 inches or between about 0.08 inches and about 0.1 inches. In still other embodiments, the diameter of the liquid inlet holes 46 is about 0.0625 inches, about 0.0125 inches, or about 0.25 inches.

In some embodiments of the invention the number of liquid inlet holes 46 is from 1 to 6. In other embodiments, the number of liquid inlet holes 46 is from 2 to 5 or from 3 to 5. In certain embodiments, the number of liquid inlet holes 46 is 1, 2, 3, 4, 5, or 6.

In some embodiments of the invention, the width of the channel 50 between the inner sleeve 41 and the outer sleeve 42 is between about 0.025 inches and about 0.125 inches, between about 0.030 inches and about 0.010 inches or between about 0.035 inches and about 0.045 inches.

In some embodiments of the invention, the volume of the chamber 68 is between about 25 ml and about 1000 ml, between about 50 ml and about 500 ml, or between about 100 ml and about 300 ml.

In some embodiments, the apparatus comprises jet nebulizers operating at pressures between about 5 psi and about 80 psi, between about 5 psi and about 50 psi, or between about 10 psi and about 50 psi. In other embodiments of the invention, the apparatus comprises jet nebulizers operating at pressures between about 7 psi to about 30 psi, or about 8 psi to about 15 psi.

In some embodiments of the invention, the total flow rate through the apparatus is between about 0.5 L/min to about 100 L/min. In other embodiments, the total flow rate through the apparatus is between about 1 L/min and about 50 L/min, or between about 12 L/min and about 30 L/min. In still other embodiments, the total flow rate through the apparatus about 0.5 L/min, about 1 L/min, about 15 L/min, about 28.3 L/min, about 30 L/min, about 50 L/min, or about 100 L/min.

In some embodiments, the apparatus comprises two atomizer heads with an impaction surface (as shown in FIG. 6) situated beyond the exit orifices of the atomizer heads.

In some embodiments, the apparatus comprises three or more atomizer heads. In some embodiments an impaction surface is placed beyond the exit orifices of the atomizer heads.

Figure 5:
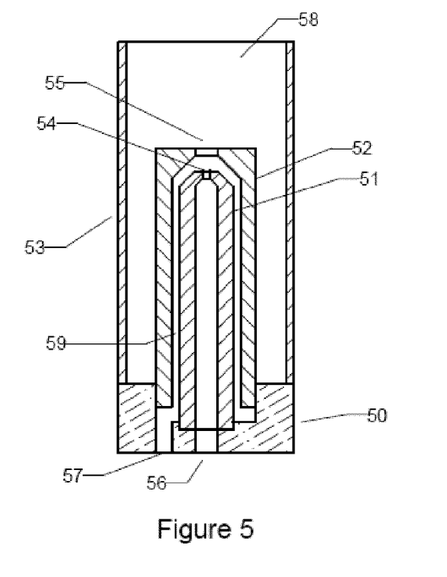
FIG. 5 shows a nebulizer head corresponding to other embodiments of the invention.

In some embodiments, the apparatus comprises a number of atomizer heads equal to the number of particle collection stages in the cascade impactor with surfaces or substrates to be coated. In some embodiments, an impaction surface is placed beyond the exit orifices of the atomizer heads FIG. 5 is a depiction of an atomizer head that uses pumped or aspirated liquid according to various embodiments of the apparatus.

In some embodiments, compressed air is introduced into the atomizer head through the inlet 56 on the atomizer base 50. The air is exhausted under pressure through a first orifice 54 and then through a second orifice 55. The coating material liquid or suspension is pumped or aspirated into inlet 57 and mixes with air between the first and second orifices 54 and 55. Aerosol is produced upon exiting the second orifice 55. An optional impaction surface (depicted in FIG. 6) may be placed just beyond the exit of the second orifice 55 to further break up the liquid droplets.

In other embodiments, inlet 57 is connected to the air source and inlet 56 is connected to the source of liquid coating material. It may be desirable to switch the inlets under conditions of high air pressure, as the expanding air jet exiting from the first orifice 54 through the second orifice 55 may produce a high suction vacuum. With certain liquid pumps, the liquid may be pumped at too high a flow rate under the high suction vacuum. In these embodiments, the air is exhausted under pressure through an orifice 55 and the coating material liquid or suspension is pumped into inlet 56 and exhausted under at least the same pressure as the air pressure and mixed between the first and second orifices 54 and 55. Aerosol is produced upon exiting the second orifice 55. An optional impaction surface (depicted in FIG. 6) may be placed just beyond the exit of the second orifice 55 to further break up the liquid droplets.

It is known in the art (Rizk, N K and A H Lefebvre, "Spray Characteristics of Plain-Jet Airblast Nebulizers", American Society of Mechanical Engineers, International Gas Turbine Conference and Exhibit, 28th, Phoenix, Ariz., Mar. 27-31, 1983) that the Sauter mean diameter of droplets produced from simple pneumatic atomizers is dependent on a number of parameters, including: air velocity, air pressure, air density, liquid density, surface tension, air to liquid ratio, and the dimensions of the atomizer (typically the air orifice diameter). If an impaction surface, such as that depicted in FIG. 6, is used downstream of the second orifice, the distance from the orifice is also a factor. Rizk and Lefebvre have shown that there is a power dependence (exponent) of mean droplet size on most of these variables. For example, the dependence of air velocity (which relates to orifice diameter and air pressure) on the mean droplet size is to the −0.80 power. Thus one of skill in the art will be able to change the mean droplet size by changing the air velocity through the atomizer. In addition, one of skill in the art will know that the mean droplet size can also be changed by varying the other parameters listed above.

The sampling size range of practical cascade impactors (e.g. Andersen Cascade Impactor, Westech, Atlanta, Ga.) is wider than the sizes produced by a single practical aerosol generator. By using more than one atomizer, and by varying the characteristics of the atomizers, a coating droplet aerosol can be produced which is sufficiently broad as to cover the wide range of particle sizes that will be collected by the cascade impactor. Thus, the coating can be applied automatically in a single application.

In some embodiments of the invention the first orifice 54 has a diameter of about 0.01 inches to about 0.1 inches. In other embodiments of the invention, the diameter of first orifice 54 is between about 0.0135 inches and about 0.08 inches, or between about 0.02 inches and about 0.05 inches.

In some embodiments of the invention the second orifice 55 has a diameter of about 0.012 inches to about 0.5 inches. In other embodiments of the invention, the diameter of second orifice 55 is between about 0.02 inches and about 0.2 inches, or between about 0.025 inches to about 0.1 inches, or between about 0.03 inches to about 0.05 inches.

In some embodiments of the invention the diameter of the second orifice 55 is defined in terms of the ratio of the second orifice 55 diameter to the first orifice 54 diameter. In some embodiments of the invention the ratio of the second orifice diameter to the first orifice diameter is between about 1 and about 5. In other embodiments, the ratio of the second orifice diameter to the first orifice diameter is between about 1.5 to about 5.0, between about 1.5 to about 3.0, or between about 1.8 to about 2.4. In still other embodiments, ratio of the second orifice diameter to the first orifice diameter is about 1, about 1.5, about 2, about 2.5, about 3, about 3.5, about 4, about 4.5, or about 5.

In some embodiments of the invention, the width of the channel 59 between the inner sleeve 51 and the outer sleeve 52 is between about 0.025 inches and about 0.125 inches, between about 0.030 inches and about 0.100 inches or between about 0.05 inches and about 0.075 inches.

In some embodiments of the invention, the volume of the chamber 68 is between about 25 ml and about 1000 ml, between about 50 ml and about 500 ml, or between about 100 ml and about 300 ml.

In some embodiments, the apparatus comprises jet nebulizers operating at pressures between about 5 psi and about 80 psi, between about 5 psi and about 50 psi, or between about 10 psi and about 50 psi. In other embodiments of the invention, the apparatus comprises jet nebulizers operating at pressures between about 7 psi to about 30 psi, or about 8 psi to about 15 psi.

In some embodiments of the invention, the total flow rate through the apparatus is between about 0.5 L/min to about 100 L/min. In other embodiments, the total flow rate through the apparatus is between about 1 L/min and about 50 L/min, or between about 12 L/min and about 30 L/min. In still other embodiments, the total flow rate through the apparatus about 0.5 L/min, about 1 L/min, about 15 L/min, about 28.3 L/min, about 30 L/min, about 50 L/min, or about 100 L/min.

In some embodiments, the apparatus comprises two atomizer heads with an impaction surface situated beyond the exit orifices of the atomizer heads.

In some embodiments, the apparatus comprises three or more atomizer heads.

In some embodiments an impaction surface is placed beyond the exit orifices of the atomizer heads.

In some embodiments, the apparatus comprises a number of atomizer heads equal to the number of particle collection stages in the cascade impactor with surfaces or substrates to be coated.

In some embodiments, an impaction surface is placed beyond the exit orifices of the atomizer heads.

In some embodiments of the apparatus, multiple atomizer heads of the design depicted in FIGS. 4 and 5 are combined to achieve a multimodal size distribution of the coating material aerosol droplets.

In some embodiments, an impaction surface is placed beyond the exit orifices of the atomizer heads.

Figure 6A:
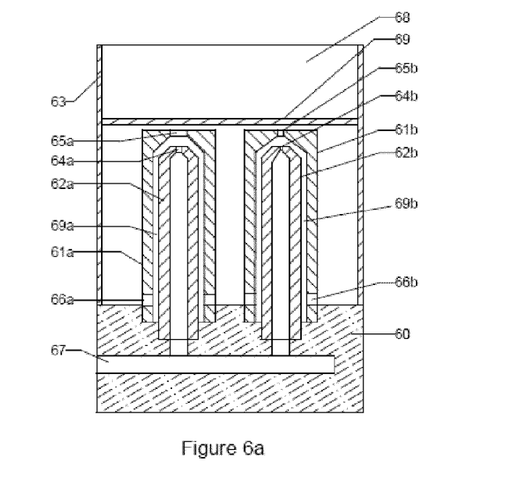
FIG. 6a is a longitudinal view.
Figure 6B:
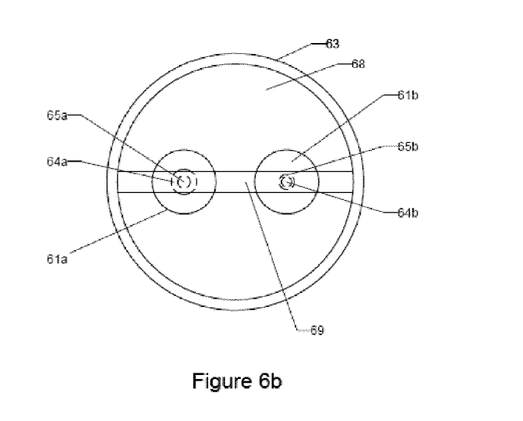
FIG. 6b is a transverse view.

FIG. 6 shows an embodiment using two atomizer heads and an optional impaction surface placed just beyond the exit orifices of the atomizer heads. FIG. 6A is a longitudinal view of two atomizer heads with an impaction surface 69 just beyond the exit orifices 65a and 65b. The impaction surface can be constructed from a rod, sheet, or plate of material. FIG. 6B is a transverse view indicating the alignment of the impaction surface 69 with the exit orifices 65a and 65b.

The coating material liquid or suspension is placed in the atomization chamber 68. Compressed air is introduced into the atomizer head through the inlet 67 on the atomizer base 60. The air is exhausted under pressure through first orifices 64a and 64b and then through second orifices 65a and 65b. The coating material liquid or suspension is aspirated through the liquid inlet holes 66a and 66b in the outer sleeves 61a and 61b of the atomizer heads. The action of the air expanding through the first orifices 64a and 64b of the inner sleeve 62a and 62b aspirates liquid into the space between the first and second orifices. Air and liquid are mixed in the space and atomized upon exit from the atomizer head through the second orifice. An impaction surface 69 is placed just beyond the exits of the second orifices to further break up the liquid droplets. The coating material aerosol is conveyed from the chamber 68 to a cascade impactor having collection surfaces in need of coating.

In some embodiments of the invention the first orifices 64a and 64b have different diameters ranging between about 0.01 inches to about 0.1 inches. In other embodiments of the invention, the first orifices 64a and 64b have different diameters between about 0.0135 inches and about 0.08 inches or about 0.02 inches and about 0.05 inches.

In some embodiments of the invention the second orifices 65a and 65b have different diameters ranging between about 0.012 inches to about 0.5 inches. In other embodiments, the second orifices 65a and 65b have different diameters ranging between about 0.02 inches and about 0.2 inches, or between about 0.025 inches to about 0.1 inches, or between about 0.03 inches to about 0.05 inches.

In some embodiments of the invention the liquid inlet holes 66a and 66b have diameters between about 0.05 inches and about 0.25 inches. In other embodiments, the diameter of the liquid inlet holes 66a and 66b is between about 0.0625 inches and 0.125 inches or between about 0.08 inches and about 0.1 inches. In still other embodiments, the diameter of the liquid inlet holes 66a and 66b is about 0.0625 inches, about 0.0125 inches, or about 0.25 inches.

The liquid inlet holes may have the same or different diameters depending upon the desired flow rate of coating liquid. The number and diameter of liquid inlet holes 66a and 66b may be easily determined by one skilled in the art to achieve sufficient atomization of the coating aerosol material. In general there will need to be enough liquid inlet holes to ensure that liquid flow is not restricted into the channels 69a and 69b. In general, the area of the liquid inlet holes needs to be larger than the respective annular areas between the inner sleeves 62a and 62b and the outer sleeves 61a and 61b. In some embodiments of the invention the number of liquid inlet holes 66a and 66b on each atomizer head is from 1 to 6. In other embodiments, the number of liquid inlet holes 66a and 66b on each atomizer head is from 2 to 5 or from 3 to 5. In certain embodiments, the number of liquid inlet holes 66a and 66b one each atomizer head is 1, 2, 3, 4, 5, or 6.

In some embodiments of the invention, the width of the channels 69a and 69b between the inner and outer sleeves between about 0.025 inches and about 0.125 inches, between about 0.030 inches and about 0.010 inches or between about 0.035 inches and about 0.045 inches. Each channel 69a and 69b may have a different width as appropriate to aspirate fluid at the desired rate. One of skill in the art will readily understand how to choose and adjust this width.

In some embodiments, the apparatus comprises jet nebulizers operating at pressures between about 5 psi and about 80 psi, between about 5 psi and about 50 psi, or between about 10 psi and about 50 psi. In other embodiments of the invention, the apparatus comprises jet nebulizers operating at pressures between about 7 psi to about 30 psi, or about 8 psi to about 15 psi. In some embodiments, the nebulizers are operating at the same pressure. In other embodiments, the nebulizers are operating at different pressures.

In some embodiments of the invention, the volume of the chamber 68 is between about 25 ml and about 1000 ml, between about 50 ml and about 500 ml, or between about 100 ml and about 300 ml.

In some embodiments of the invention, the total flow rate through the apparatus is between about 0.5 L/min to about 100 L/min. In other embodiments, the total flow rate through the apparatus is between about 1 L/min and about 50 L/min, or between about 12 L/min and about 30 L/min. In still other embodiments, the total flow rate through the apparatus about 0.5 L/min, about 1 L/min, about 15 L/min, about 28.3 L/min, about 30 L/min, about 50 L/min, or about 100 L/min.

In some embodiments, the apparatus comprises two atomizer heads with an impaction surface situated beyond the exit orifices of the atomizer heads.

In some embodiments, the apparatus comprises three or more atomizer heads. In some embodiments an impaction surface is placed beyond the exit orifices of the atomizer heads.

In some embodiments, the apparatus comprises a number of atomizer heads equal to the number of particle collection stages in the cascade impactor with surfaces or substrates to be coated. In some embodiments, an impaction surface is placed beyond the exit orifices of the atomizer heads.

EXAMPLES

The following examples are intended to be illustrative of various embodiments of the apparatuses and methods of the invention and are not intended to be limiting in nature.

Example 1

An embodiment of the invention with two atomizer heads was constructed. The atomizer heads were configured with a particle impaction surface as shown and described in FIG. 6. The dimensions of the first orifices of the two atomizer heads were 0.0178 and 0.0410 inches, respectively. For both atomizer heads, the ratio of the diameter of the second orifice to the first orifice was about 2.0. The dimension of the liquid channel in the two atomizer heads was about 0.069 inches. Four holes were used in each outer sleeve to allow the liquid coating material to be aspirated into the atomizers. The impaction surface was located 0.035 inches away from the exits of the second orifices. A solution of silicone Antifoam (Dow Corning 1520) was prepared as a 1:10 dilution in water and labeled with 0.01% ammonium fluorescein to assist in visualization and chemical analysis. 3.2 ml of the solution was added to the atomizer chamber.

Example 2

An eight-stage Andersen cascade impactor (Westech Instruments, Atlanta, Ga.) was assembled with clean, uncoated collection plates according to the manufacturer's instructions. The atomizer heads in the embodiment described in Example 1 were operated at 8.2 psi for about 1.5 minutes. At that pressure, the total airflow was approximately 30 lpm. The coating aerosol droplets were directed to the inlet of the Andersen impactor. The outlet of the impactor, which in normal operation according to the manufacturer's instructions is connected to a vacuum source, was left open to the atmosphere to allow the coating aerosol droplets to flow through the device. Following atomization of the coating material, clean, dry air was passed through the impactor for 8 minutes to evaporate residual solvent and dry the coating material.

Example 3

The impactor was disassembled and the particle collecting plates were visually observed and photographed to ascertain the uniformity of the coating material in the particle collecting regions of the impactor plates. The amount of coating material deposited was determined chemically by assaying the fluorescein tracer with a Turner Biosystems Picofluor fluorometer (Sunnyvale, Calif.). Visual inspection showed uniformity of the deposited coating material in the particle collecting regions of the impactor plate. Table 1 gives the total amount of grease deposited on each of the stages. The results show a sufficient amount of material deposited in the particle collecting regions of each stage.

TABLE 1

Amount of Grease [mg] Deposited on Each Particle Collection Surface of the Andersen Cascade Impactor

| Stage No. | Quantity of Antifoam Deposited [mg] |
| --- | --- |
| 0 | 0.27 |
| 1 | 0.29 |
| 2 | 0.15 |
| 3 | 0.27 |
| 4 | 0.47 |
| 5 | 2.18 |
| 6 | 1.41 |
| 7 | 0.67 |

Example 4

A set of clean dry Andersen impactor collection plates is coated with a 1:10 dilution of silicone Antifoam (Dow Corning 1520) in water Coating of the plates is achieved by flooding the surface with the liquid dispensed from a pipette and allowing it to dry. This is one of the many traditional methods used to coat plates outside of an impactor prior to assembly and sampling.

Example 5

An aerosol of ammonium fluorescein is produced in a wind tunnel by nebulizing a 5% aqueous ammonium fluorescein solution with an Aeroneb nebulizer (Nectar, San Carlos, Calif.) and allowed to dry to solid particles in the wind tunnel.

Ammonium fluorescein is chosen because of its widespread and long-known use in the art as a sensitive tracer material. It is very soluble in water, forms non-hygroscopic particles, and is easily analyzed with a spectrometer or a fluorometer down to a concentration of 1 nanogram per milliliter.

The dried aerosol is sampled from the wind tunnel with the Andersen cascade impactor prepared as described in Example 4 and the mass of aerosol deposited on each stage is analyzed with a Turner Biosystems Picofluor fluorometer (Sunnyvale, Calif.).

Example 6

The same aerosol as described in Example 5 is also sampled into an Andersen impactor whose plates are coated according to an embodiment of the invention as described in Example 2. In this instance, however, the coating aerosol does not have the 0.01% ammonium fluorescein added to it.

The size distributions as measured by both impactor samples are plotted on a log-probability scale and indicate very good agreement, within experimental error, between the two test methods, and thus the two methodologies for coating the collection substrates.

Example 7

An embodiment of the apparatus comprising the atomizer head described in FIG. 5 is constructed with the first orifice diameter of 0.06 inches and the second orifice diameter 0.12 inches. The liquid channel width is about one-sixteenth (1/16) inches. A solution of silicone Antifoam (Dow Corning 1520) was prepared as a 1:10 dilution in water and labeled with 0.01% ammonium fluorescein to assist in visualization and chemical analysis. Compressed air at a pressure of 15 psi is applied to the atomizer head. The diluted Antifoam solution is pumped into the atomizer at flow rates of 0.5 cc/min, 1 cc/min, 2 cc/min, 3 cc/min, and 4 cc/min for 15 to 20 seconds at each flow rate. The aerosol exiting the apparatus is directed to the inlet of an Andersen cascade impactor containing clean particle collecting plates. The outlet of the impactor is left open to the atmosphere.

After generating coating aerosol at all of the indicated liquid flow rates, the impactor is disassembled and the particle collecting plates are visually observed and photographed to ascertain the uniformity of the coating material in the particle collecting regions of the impactor plates. The amount of coating material deposited is determined chemically by assaying the fluorescein tracer with a Turner Biosystems Picofluor fluorometer (Sunnyvale, Calif.). Visual inspection shows uniformity of the deposited coating material in the particle collecting regions of the impactor plate. Chemical analyses show adequate deposits across all stages.

Example 8

A clean set of Andersen impactor collection plates was prepared and coated according to Example 4. Ammonium fluorescein aerosol was produced and sampled according to Example 5. Three repetitions of this measurement were made.

The aerosol as described in Example 5 was also sampled into an Andersen cascade impactor whose plates were coated according to an embodiment of the invention as described in Example 2. In this instance, the coating aerosol did not have the 0.01% ammonium fluorescein added to it.

Figure 7:
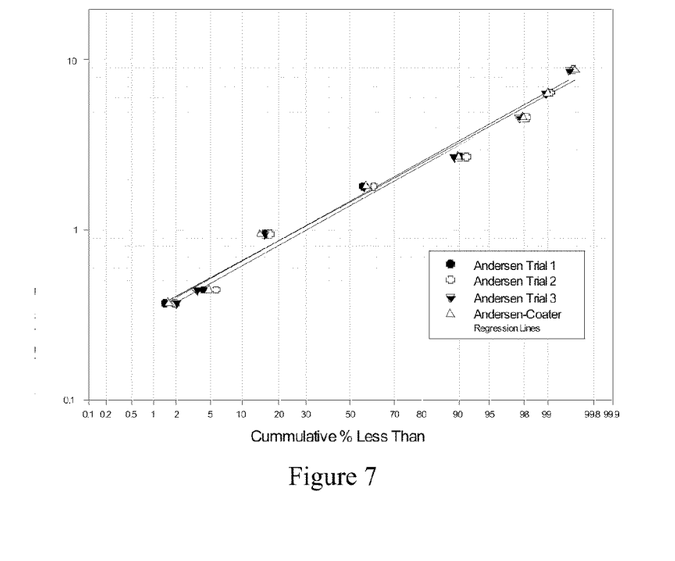
FIG. 7 shows the results of aerosol measurements made with impactors coated by traditional substrate coating method and by an embodiment of the apparatus and methods described herein.

The size distributions as measured by impactors with particle collection plates coated according to Example 4 and Example 2 were plotted on a log-probability scale (FIG. 7). The results show very good agreement, within experimental error, between the two test methods and thus the two methodologies for coating the collection substrates.

Example 9

An embodiment of the apparatus comprising the atomizer head described in FIG. 5 was constructed with the first orifice diameter of 0.035 inches and the second orifice diameter 0.046 inches. Inlet 57 was connected to the air source and inlet 56 was connected to the source of liquid coating material The air channel width was about one-sixteenth (1/16) inches. A solution of silicone Antifoam (Dow Corning 1520) was prepared as a 1:10 dilution in water and labeled with 0.01% ammonium fluorescein to assist in visualization and chemical analysis. Compressed air at a pressure of 17 psi was applied to the atomizer head. The diluted Antifoam solution was pumped into the atomizer at flow rates of 0.65 cc/min, 2.1 cc/min, and 4.2 cc/min for 2 minutes, or 10 minutes. The aerosol exiting the apparatus was directed to the inlet of an Andersen cascade impactor containing clean particle collecting plates. The outlet of the impactor was left open to the atmosphere.

Figure 8:
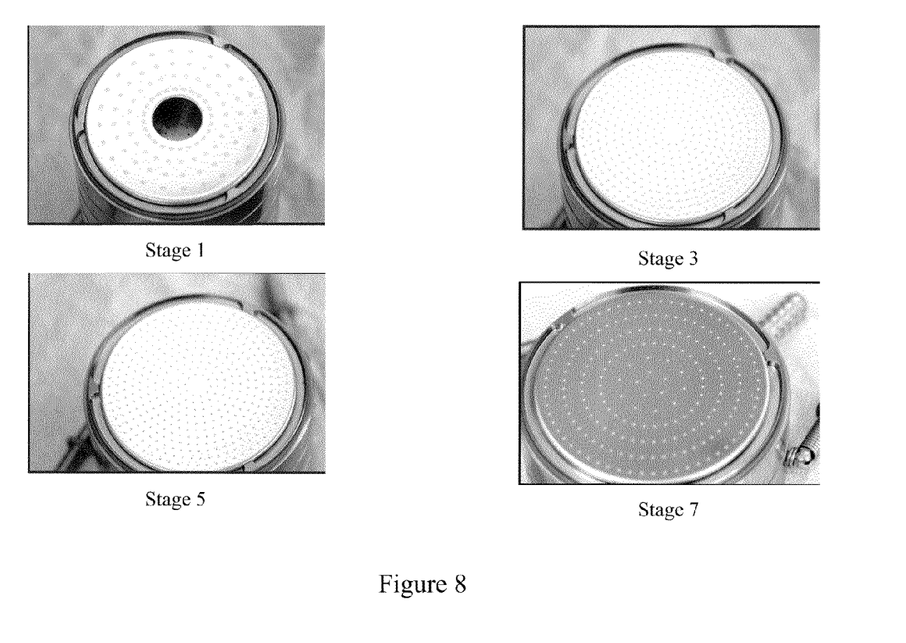
FIG. 8 shows the uniformity of localized deposition of coating material for four representative stages from an Andersen cascade impactor coated according to the embodiments and methods described herein.

After generating coating aerosol at each of the indicated liquid flow rates, the impactor was disassembled and the particle collecting plates were visually observed and photographed to ascertain the uniformity of the coating material in the particle collecting regions of the impactor plates. The amount of coating material deposited was determined chemically by assaying the fluorescein tracer with a Turner Biosystems Picofluor fluorometer (Sunnyvale, Calif.). Visual inspection showed uniformity of the deposited coating material in the particle collecting regions of the impactor plate for each atomizer liquid flow rate. FIG. 8 shows representative coating uniformity on the collection plates for stages 1, 3, 5, and 7 from an impactor coated for 2 minutes at a liquid flow rate of 4.2 cc/min. Chemical analyses showed adequate deposits (0.4 to 1.4 mg) across all stages. For all three liquid flow rates, the GSD was 2.9. The MMAD was highest (1.8 µm) for the highest liquid flow rate.

While preferred embodiments of the invention have been shown and described herein, it will be obvious to those skilled in the art that such embodiments are provided by way of example only. Numerous variations, changes, and substitutions will now occur to those skilled in the art without departing from the invention. Specific dimensions given in the above examples are for the purposes of enablement of the examples. It should be understood that various alternatives to the embodiments of the invention described herein may be employed in practicing the invention, including alterations of the above stated specific dimensions. While the examples presented have shown a certain number of aerosol generators (atomizer heads), it should be understood that additional atomizer heads may be added to increase the output and breadth of the size distribution of the coating aerosol droplets, according to the disclosures of this invention. Further, one of skill in the art would now readily recognize how to substitute any of a variety of other atomizers or aerosol generators to achieve substantially the same results of the methods and apparatus disclosed and claimed herein. It is intended that the following claims define the scope of the invention and that methods and structures within the scope of these claims and their equivalents be covered thereby.

What is claimed is:

1. An apparatus for localized coating of the collection surfaces of an assembled cascade impactor comprising a plurality of aerosol generators operating to produce coating aerosol droplets with different mass median aerodynamic diameters, wherein the aggregated output of said plurality of aerosol generators is directable to the inlet of the assembled cascade impactor, and wherein said coating is localized to the particle collecting regions of said surfaces.

2. The apparatus of claim 1 wherein said cascade impactor is connected to a vacuum source to draw said aggregated output of coating aerosol droplets through said impactor.

3. The apparatus of claim 1, wherein said mass median diameters are selected to span the range of cutoff diameters for the stages of said cascade impactor.

4. The apparatus of claim 1 wherein the said aerosol generators are jet nebulizers.

5. The apparatus of claim 4 wherein said jet nebulizers are constructed with different orifice diameters.

6. The apparatus of claim 4 wherein said jet nebulizers produce a positive pressure sufficient to force the coating aerosol droplets through said cascade impactor.

7. The apparatus of claim 1 further comprising a timer connected to a solenoid valve through which compressed air flows to said plurality of aerosol generators.

8. The apparatus of claim 7 wherein said timer is set to stop the production of aerosol when the particle collection surfaces are sufficiently coated.

9. The apparatus of claim 1 wherein the aerosol generators are selected from the group consisting of pneumatic atomizers, jet nebulizers, rotary atomizers, spinning disc aerosol generators, vibrating orifice generators, vibrating membrane generators, vibrating mesh generators, electrohydrodynamic nebulizers, electrostatic nebulizers, and combinations thereof.

10. The apparatus of claim 1 wherein additional auxiliary airflow is added to the output of said plurality of aerosol generators.

11. An apparatus for localized coating of the particle collection surfaces of an assembled cascade impactor comprising an aerosol generator operating to produce coating aerosol droplets having size distributions with different mass median aerodynamic diameters, wherein the output of said aerosol generator is directable to the inlet of the assembled cascade impactor, and wherein said coating is localized to the particle collecting regions of said surfaces.

12. The apparatus of claim 11 wherein said cascade impactor is connected to a vacuum source to sample said out put of coating aerosol droplets.

13. The apparatus of claim 11, wherein said mass median aerodynamic diameters are selected to span the range of cutoff diameters for the stages of said cascade impactor.

14. The apparatus of claim 13 wherein said aerosol generator is a jet nebulizer.

15. The apparatus of claim 14 wherein a pump is used to supply a solution or suspension of coating material to said jet nebulizer.

16. The apparatus of claim 15 wherein the delivery rate of said solution or suspension is varied with time to produce a variation in the size distribution of the coating aerosol droplets.

17. The apparatus of claim 14 wherein said jet nebulizer produces a positive pressure sufficient to force the coating aerosol droplets through said cascade impactor.

18. The apparatus of claim 14 further comprising a timer connected to the pump, wherein the timer is set to stop the pump when the particle collection surfaces are sufficiently coated.

19. A method of depositing a localized coating on the collection surfaces of an assembled cascade impactor comprising generating a multimodal coating droplet aerosol with a plurality of aerosol generators, and directing the aerosol through the impactor, wherein said coating is localized to the particle collecting regions of said surfaces of said assembled cascade impactor, and wherein the modes of said multimodal coating droplet aerosol are selected to produce droplets that span the range of cutoff diameters for the stages of said cascade impactor.

20. The method of claim 19 wherein said cascade impactor is connected to a vacuum source to sample said coating droplet aerosol.

21. The method of claim 19 wherein the modes of said multimodal coating droplet aerosol are selected to span the range of cutoff diameters for the stages of said cascade impactor.

22. The method of claim 19 wherein the aerosol generators are selected from the group consisting of pneumatic atomizers, jet nebulizers, rotary atomizers, spinning disc aerosol generators, vibrating orifice generators, vibrating membrane generators, vibrating mesh generators, electrohydrodynamic nebulizers, electrostatic nebulizers, and combinations thereof.

23. The method of claim 19 wherein the aerosol generators are jet nebulizers.

24. The method of claim 19 further comprising drying of the deposited coating with an auxiliary airflow.

25. A method for localized coating of the collection surfaces of an assembled cascade impactor comprising operating an aerosol generator to produce coating aerosol droplets having size distributions with different mass median aerodynamic diameters, and directing said droplets to the inlet of the cascade impactor, wherein said coating is localized to the particle collecting regions of said surfaces of said assembled cascade impactor.

26. The method of claim 25 wherein a vacuum is applied to the outlet of the impactor to draw the coating aerosol droplets therethrough.

27. The method of claim 25, wherein the mass median aerodynamic diameters of said size distributions are selected to span the range of cutoff diameters for the stages of said cascade impactor.

28. The method of claim 27 wherein said aerosol generator is a jet nebulizer.

29. The method of claim 28 further comprising use of a pump to supply a solution or suspension of coating material to said jet nebulizer.

30. The method of claim 29 further comprising varying the supply rate of said pump with time to produce variations in the size distribution of the coating aerosol droplets.

31. The method of claim 25 further comprising producing a positive pressure and airflow sufficient to force the coating aerosol droplets through the cascade impactor.

\* \* \* \* \*